(12) United States Patent
Vishnu Newadkar et al.

(10) Patent No.: US 8,455,655 B2
(45) Date of Patent: Jun. 4, 2013

(54) PREPARATION OF DIHYDROPYRIDINES

(75) Inventors: Ravindranath Vishnu Newadkar, Mahape (IN); Anil Purushottam Joshi, Mahape (IN); Santosh Kumar Singh, Navi Mumbai (IN)

(73) Assignee: Laboratorios Lesvi, S.L., Barcelona (ES)

( * ) Notice: Subject to any disclaimer, the term of this patent is extended or adjusted under 35 U.S.C. 154(b) by 117 days.

(21) Appl. No.: 13/102,101

(22) Filed: May 6, 2011

(65) Prior Publication Data

US 2011/0275825 A1    Nov. 10, 2011

Related U.S. Application Data

(60) Provisional application No. 61/332,446, filed on May 7, 2010.

(51) Int. Cl.
*C07D 213/803*    (2006.01)

(52) U.S. Cl.
USPC .......................................................... 546/321

(58) Field of Classification Search
None
See application file for complete search history.

(56) References Cited

U.S. PATENT DOCUMENTS 5,856,346 A    1/1999    Andersson
6,350,877 B1   2/2002    Mattson

FOREIGN PATENT DOCUMENTS

WO    WO 9512578    5/1995
WO    WO 0031035    6/2000

*Primary Examiner* — Zinna Northington Davis
(74) *Attorney, Agent, or Firm* — Merchant & Gould P.C.

(57) ABSTRACT

The invention relates to a method and compounds for the preparation of clevidipine butyrate, a very short acting hypertensive calcium antagonist, as well as the synthesis of these compounds useful for the preparation of clevidipine (also known as clevidipine butyrate). Moreover the invention also discloses polymorphic forms of clevidipine butyrate, useful for the preparation of pharmaceutical compositions, and processes to prepare them.

15 Claims, 4 Drawing Sheets

PREPARATION OF DIHYDROPYRIDINES

PRIORITY

Priority is claimed to U.S. 61/332,446, filed on May 7, 2010, the subject matter of which is incorporated by reference.

FIELD OF THE INVENTION

This invention relates to an improved method for the preparation of clevidipine, also known as clevidipine butyrate, a very short acting hypertensive calcium antagonist, as well as the synthesis of new compounds useful for the preparation of clevidipine.

BACKGROUND OF THE INVENTION

Clevidipine butyrate is a dihydropyridine calcium channel blocker, currently indicated for the reduction of blood pressure, when oral therapy is not feasible or not desirable. Its chemical name is butyroxymethyl 4-(2,3-dichlorophenyl)-2,6-dimethyl-1,4-dihydropyridine-3,5-dicarboxylate and its chemical structure is depicted below:

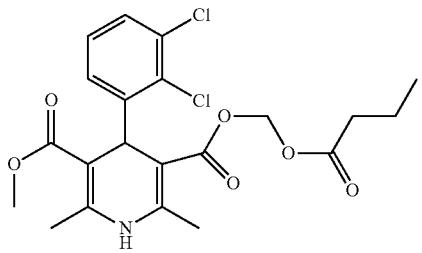 [SMILES: CCCC(=O)OCOC(=O)C1=C(C)NC(C)=C(C(=O)OC)C1c1cccc(Cl)c1Cl]

It is commercialized under the brand name of Cleviprex®, as a racemic mixture, in which each enantiomer has antihypertensive activity. Cleviprex® is an emulsion, suitable for intravenous applications.

Clevidipine butyrate was first described in WO 95/12578 (U.S. Pat. No. 5,856,346), as a very useful short-acting steerable antihypertensive drug, for intravenous administration.

WO 95/12578 discloses a method for preparing clevidipine butyrate from 1,4-dihydro-2,6-dimethyl-4-(2',3'-dichlorophenyl)-5-carboxymethyl-3-pyridinecarboxylic acid and chloromethyl butyrate. This route has several drawbacks. Firstly, the purification of the final product is carried out by chromatographic methods, which are generally expensive, environmentally unfriendly and time consuming, therefore not recommended for industrial application. A second negative aspect is the nature of the solvent used. WO 95/12578 teaches that the reaction must be carried out in DMF or acetonitrile, both polar aprotic solvents, therefore reducing significantly the number of industrially suitable solvents. For instance, acetonitrile, the solvent used in patent application WO 00/31035 (U.S. Pat. No. 6,350,877), has suffered a worldwide commercial shortage over the last few years. Moreover, DMF, a solvent considered as a possible carcinogen by the International Agency for Research on Cancer (IARC), has been linked to cancer in humans and to cause birth defects.

Additionally, the inventors have found that in order to achieve the purity requirements needed for an injectable formulation, the product as obtained in the WO 95/12578 would have to be purified further.

WO 00/31035 seeks to reduce some of the drawbacks associated with the process disclosed in the WO 95/12578. The improvement is related to the use of the sodium and potassium salt of the 4-(2',3'-dichlorophenyl)-1,4-dihydro-5-methoxycarbonyl-2,6-dimethyl-3-pyridinecarboxylate, instead of the acid form previously described. The improved process is depicted below:

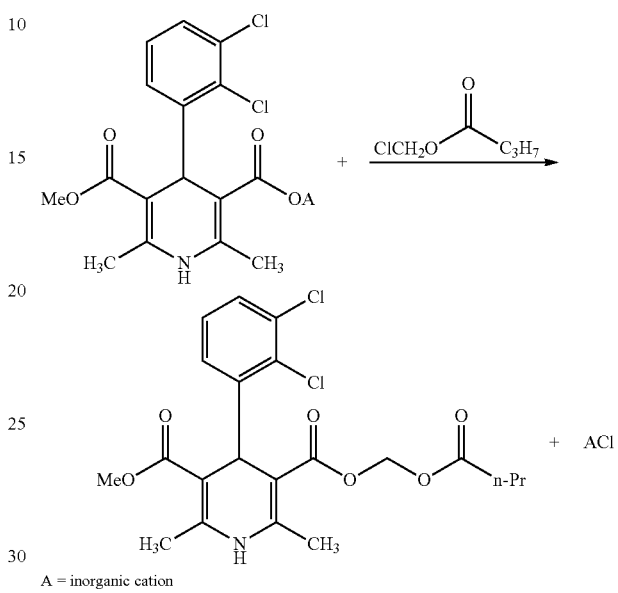

A = inorganic cation

Although said process offers some improvements over the prior art, it still has some limitations. Similarly to WO 95/12578, chloromethyl butyrate is also used in the last reaction step. According to the material safety data sheet of chloromethyl butyrate, it is corrosive, flammable and it can cause eye burns, skin burns, gastrointestinal tract burns and chemical burns to the respiratory tract. Therefore, its use increases the production costs as it is necessary use special equipment and manufacturing facilities. The use of chloromethyl butyrate should be avoided in the last steps of synthetic processes, where the equipment is more expensive. The excess use of chloromethyl butyrate would lead to the generation of additional impurities similar in nature to the final product. It is well known in the art, that the more similar two compounds are, the more difficult the purification is. Consequently, clevidipine butyrate, directly obtained by the processes disclosed in WO 00/31035, would have to be further purified in order to be used in the manufacture of pharmaceutical compositions. This mandatory extra purification step is time consuming and difficult to be carried out on an industrial scale. In any case, this approach will lead to the formation of at least one equivalent of sodium chloride, which will have to be removed.

Equally to WO 95/12578, the last step to obtain clevidipine butyrate is limited to the use of a polar aprotic solvent reducing significantly the number of industrially suitable solvents. Since the last reaction step takes place in acetonitrile and being clevidipine butyrate soluble in said solvent, a solvent-exchange must be performed in order to isolate clevidipine butyrate in a solid form from the reaction media.

Moreover, the process disclosed in WO 95/12578 implies the use of the cyanide intermediate, cyanoethyl methyl 4-(2',3'-dichlorophenyl)-2,6-dimethyl-1,4-dihydropyridine-3,5-dicarboxylate, to obtain the dihydropyridine carboxylate salt.

As it is well known in the art, many cyanide-containing compounds are toxic, since they can readily release hydrogen cyanide (HCN) or cyanide ions. Both, HCN or the cyanide ions, are highly toxic to animals and human beings. The cyanide group is introduced as a protecting group. This means that the use of the cyanide intermediate leads to an increase of the number of manufacturing steps (protection followed by deprotection and purification) to prepare clevidipine butyrate. Although the yield disclosed for the last synthetic steps is relatively high, as a result of the increased number of manufacturing steps, the overall yield will not be that high when the overall synthesis (starting from the raw materials) is taken into consideration.

In accordance with health registration requirements of the U.S. and international health registration authorities, e.g. the FDA's Good Manufacturing Practices ("GMP") requirements, when preparing pharmaceutical compositions containing clevidipine butyrate for administration to mammals, there is a need to produce crystalline forms, or polymorphs, of clevidipine butyrate as pure as possible. Especially important are those forms, which have constant physical properties. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph.

SUMMARY OF THE INVENTION

Disclosed herein is a process for the synthesis of clevidipine butyrate wherein the clevidipine butyrate is directly obtained in a high purity and yield. The process for the preparation of clevidipine butyrate comprises the reaction of methyl 3-amino crotonate with benzylidine butyrate, compound of formula (I):

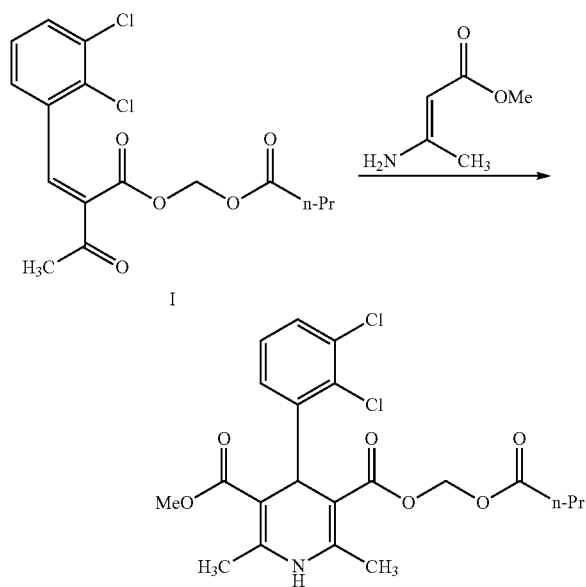

in the presence of at least an organic solvent or a solvent mixture comprising an organic solvent. The disclosed process is versatile enough, and it is not restricted to a specific kind of solvent. Therefore, if desired it is possible to carry out the reaction in a solvent where the clevidipine butyrate could be directly crystallized from, or in a solvent having low toxicity.

The starting materials for the last steps and co-reactants are non-toxic and they are either commercially available or obtained with less synthetic steps compared with the processes disclosed in the art. The impurities identified for the process are easily removed by the techniques commonly used at industrial scale.

Also disclosed herein are compounds 2-(2',3'-dichlorobenzylidene)-3-oxo-butyric acid and 2-(2',3'-dichloro-benzylidene)-3-oxo-butyric acid butyryloxymethyl ester and their preparation as well as their use as intermediates for the preparation of clevidipine butyrate. These intermediate compounds are obtained in high purity and yield and can be easily isolated and purified by using standard industrial methods, avoiding the use of column chromatography. Moreover, the disclosed process permits the isolation of some of the intermediates, which is a clear advantage, as it is explained below.

The disclosed process provides for an additional aspect which relates to the discovery of crystalline forms of clevidipine butyrate and their method for preparing thereof, which are useful to improve the pharmaceutical performance of pharmaceutical products.

DEFINITIONS

Figure 1:
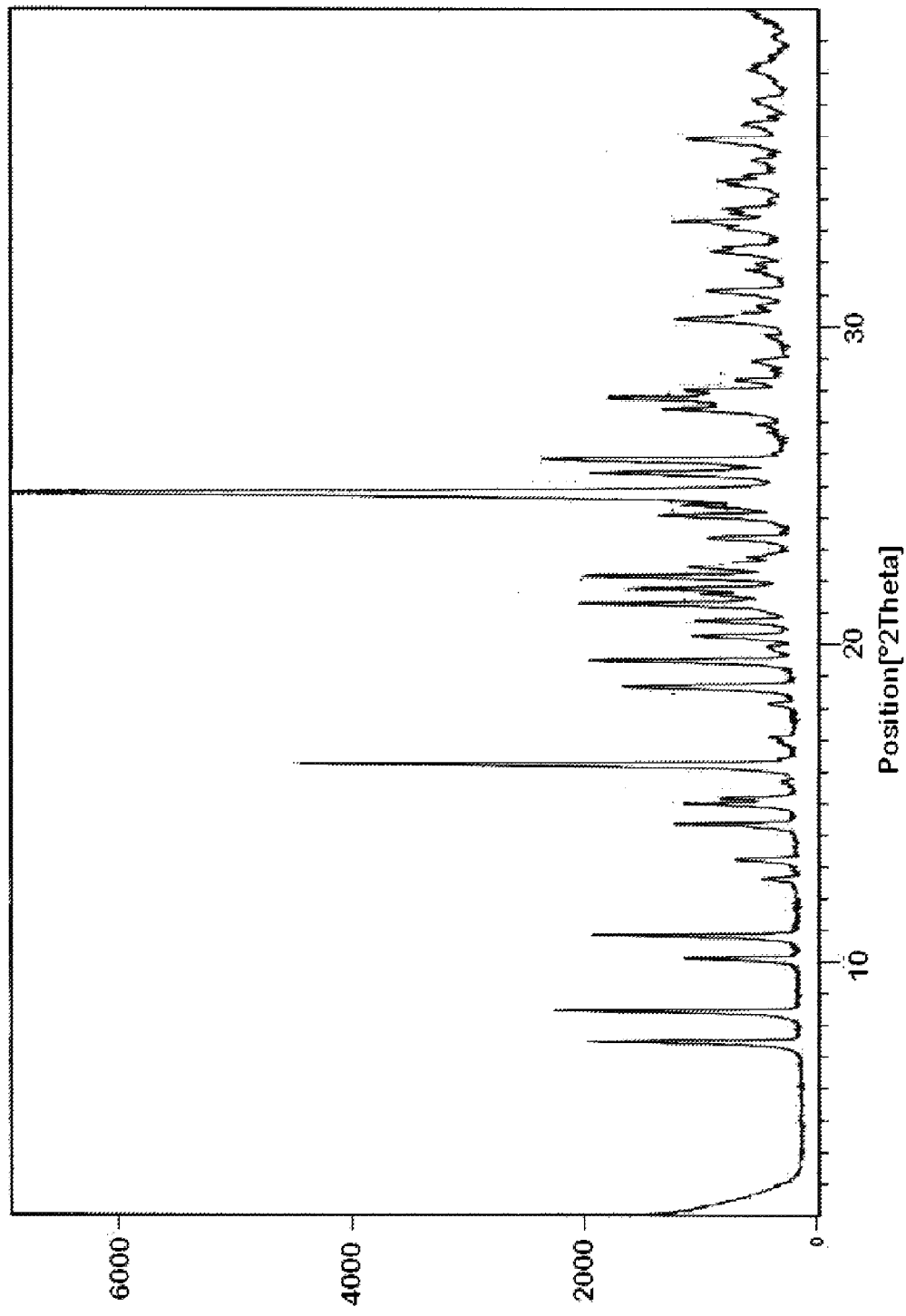
FIG. 1: XRD of clevidipine butyrate form A.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not.

The term "about" means that the recited numerical value is part of a range that varies within standard experimental error.

The term "leaving group" refers to a chemical group capable of being displaced by a nucleophile. The structure of the leaving group will depend, in part, on the general reaction conditions employed such as structure of the nucleophile, solvent, temperature and time, all within the knowledge and control of the skilled artisan. Examples of leaving groups commonly employed include sulfonyl esters such as trifluoromethylsulfonyl, para-nitrobenzenesulfonyl, para-toluenesulfonyl, methylsulfonyl and the like; carboxyl esters such as trifluoroacetyl, para-nitrobenzoyl, para-methylbenzoyl, acetyl and the like; and halogens such as iodo, bromo, chloro, fluoro and the like. In J. March Advanced Organic Chemistry, 4th edition, 1992, are listed some typical leaving groups. In the context of the disclosed process, the leaving groups are selected from halogens and sulfonyloxy groups. The halogens include fluorine, chlorine, bromine and iodine. In a sub-aspect, halogen is chlorine. The sulfonyloxy group is represented by —$OSO_2R_2$, wherein $R_2$ is a substituted or un-substituted linear or branched $C_1$-$C_{10}$ alkyl, a substituted or unsubstituted aryl, such as phenyl, benzyl, tolyl, o-xylyl, a fluorinated $C_1$-$C_{10}$ linear, branched or cyclic hydrocarbon or a halogen. In one aspect, $R_2$ is methyl, p-toluoyl, trifluoromethyl, or fluorine.

As used herein, the term "organic solvent" refers to "a component of a solution which is present in excess, or whose physical state is in the same as that of the solution". Normally the term "organic solvent" includes any substance containing carbon, hydrogen and optionally, oxygen and is normally a liquid at 25° C. or is easily converted to a liquid by elevating the temperature up to 100° C. In addition, the term organic solvent further refers to a combination of two or more of these substances mixed together.

Any solvent having the above described properties can be employed in the disclosed process. Examples of solvent classes useful herein include, but are not limited to, alcohols, alkoxylated alcohols, aryloxylated alcohols, polyols, glyceryl esters, polymeric ethers, ketones, hydrocarbons and mixtures thereof.

Suitable solvents are benzyl alcohol, benzyl benzoate, 2-benzyloxyethanol, benzyl glycol, 1,2-butanediol, 1,3-butanediol, 1,4-butanediol, 2,3-butanediol, butoxyethyl acetate (regular), butyl acetate, t-butyl acetate, n-butanol, t-butanol, butylene glycol, butylene glycol proprionate, butyloctanol, butyloctyl benzoate, $C_{7-8}$ Isoparaffin, $C_{8-9}$ Isoparaffin, $C_{9-11}$ Isoparaffin, $C_{9-13}$ isoparaffin, cyclohexanedimethanol, cyclohexanone, decane, 1,10-decanediol, diethoxydiglycol, dimethyl glutarate, dimethyl maleate, dioxolane, dipropylene glycol, dipropylene glycol dimethyl ether, dipropyl oxalate, ethoxydiglycol, ethoxydiglycol acetate, ethyl acetate, ethylene glycol, ethylene glycol mono-n-butyl ether, ether hexanediol, ethylhexyl acetate, ethylhexyl benzoate, ethyl lactate, glycerine, hexane, hexandiol, 1,2-hexanediol, 1,2,6-hexanetriol, hexylene glycol, isobutoxypropanol, isododecane, isopentyldiol, isopropyl acetate, isopropyl alcohol (IPA), 3-methoxybutanol, methoxybutanol, methoxyethanol, methoxyisopropanol, methoxymethylbutanol, methyl acetate, methyl hexyl ether, pentylene glycol, 2-phenoxyethanol, 1-phenoxy-2-propanol, 2-phenyethanol, propanediol, propyl acetate, propyl alcohol, propylene glycol, trimethyl-1,3-pentanediol, acetone, methyl ethyl ketone (MEK), methyl isobutyl ketone (MIBK), methyl tert butyl ether, ethyl acetate, methyl acetate, propyl acetate, isopropyl acetate, butyl acetate, isobutyl acetate, diisopropyl ether (DIPE), toluene, methyl cyclohexane, and xylene.

In one aspect, the organic solvents useful herein have a molecular weight of about 200 or less. In another aspect the organic solvents have a molecular weight of about 185 or less. In yet another aspect, the organic solvents have a molecular weight of about 160 or less.

As used herein, the term "base" refers to a substance that tends to accept a proton. Typical bases are inorganic or organic.

An inorganic base is a substance, which contains a metal cation and does not contain an organic moiety, as compared to an organic base, which is a substance that contains an organic moiety. Typical inorganic bases are for example, a metal hydroxide, such as sodium hydroxide and potassium hydroxide, metal carbonates, such as sodium carbonate and potassium bicarbonate.

An organic base is a substance which contains an organic moiety comprising a nitrogen atom. Typical organic bases are, for example, an amine (R'R"R'"N) or a heterocycle.

Amines can be represented by the structure R'R"R'"N. In a first instance of R'R"R'"N, each R', R", and R'" is independently selected from hydrogen, a linear alkyl, and a cycloalkyl, which includes, but is not limited to N,N-diisopropylethylamine, diethylamine, triethylamine, etc. In a second instance of R'R"R'"N, R' is selected from hydrogen and alkyl and each of R" and R'" are a part of a cyclic ring system, including but not limited to piperidine, morpholine, etc.

Heterocycles include, but are not limited to, pyridine, collidine, 2,6-($C_{1-6}$alkyl)-pyridine, 4-dimethylamino-pyridine (DMAP), imidazole, N-methyl-imidazole, pyrazole, N-methyl-pyrazole, etc.

As used herein, the term "acid" refers to a substance that tends to release a proton. The term "acid" contemplates all inorganic or organic acids. Acids include, but are not limited to, mineral acids, such as hydrogen halides and their solutions (hydrochloric acid (HCl), hydrobromic acid (HBr), hydroiodic acid (HI)), hypochloric acid (HClO), chloric acid ($HClO_3$), perchloric acid ($HClO_4$), hypobromous acid (HBrO), bromic acid ($HBrO_3$), perbromic acid ($HBrO_4$), hyopiodous acid (HIO), iodic acid ($HIO_3$), periodic acid ($HIO_4$), sulfuric acid ($H_2SO_4$), nitric acid ($HNO_3$), phosphoric acid ($H_3PO_4$), fluoroboric acid, sulfonic acids, such as methanesulfonic acid (or mesylic acid, $CH_3SO_3H$), ethanesulfonic acid (or esylic acid, $CH_3CH_2SO_3H$), benzenesulfonic acid (or besylic acid, $C_6H_5SO_3H$), p-toluenesulfonic acid (or tosylic acid, $CH_3C_6H_4SO_3H$), trifluoromethanesulfonic acid (or triflic acid, $CF_3SO_3H$), carboxylic acids, such as acetic acid, trifluoroacetic, citric acid, formic acid, gluconic acid, lactic acid, oxalic acid, tartaric acid, succinic acid, and malic acid.

The term "phase transfer catalyst" is used herein to represent any catalyst which can effectively facilitate the transfer of ions or other reactive or functional chemical species or groups across the phase interface.

The term "purification" refers to the process wherein a purified drug substance can be obtained. The term "industrial purification" refers to purifications which can be carried out on an industrial scale such as solvent extraction, filtration, slurring, washing, phase separation, evaporation, centrifugation or crystallization.

As used herein, the term, "solvent extraction" refers to the process of separating components of a mixture by using a solvent which possesses greater affinity for one component, and may therefore separate said one component from at least a second component which is less miscible than said one component with said solvent.

The term "filtration" refers to the act of removing solid particles greater than a predetermined size from a feed comprising a mixture of solid particles and liquid. The expression "filtrate" refers to the mixture less the solid particles removed by the filtration process. It will be appreciated that this mixture may contain solid particles smaller than the predetermined particle size. The expression "filter cake" refers to residual solid material remaining on a feed side of a filtration element.

As used herein, the term "slurring" refers to any process which employs a solvent to wash or disperse a crude product.

As used herein, the term "washing" refers to the process of purifying a solid mass (e.g., crystals) by passing a liquid over and/or through the solid mass, as to remove soluble matter. The process includes passing a solvent, such as distilled water, over and/or through a precipitate obtained from filtering, decanting, or a combination thereof. For example, in one aspect of a disclosed embodiment, washing includes contacting solids with solvent or solvent mixture, vigorously stirring (e.g., for two hours), and filtering. The solvent can be water, can be an aqueous solvent system, or can be an organic solvent system. Additionally, the washing can be carried out with the solvent having any suitable temperature. For example, the washing can be carried out with the solvent having a temperature between about 0° C. and about 100° C.

The term "phase separation" refers to a solution or mixture having at least two physically distinct regions.

The term "evaporation" refers to the change in state of solvent from liquid to gas and removal of that gas from the reactor. Generally gas is removed by vacuum applied across the membrane. Various solvents may be evaporated during the synthetic route disclosed herein. As known to those of skill in the art, each solvent may have a different evaporation time and/or temperature.

The term "crystallization" refers to any method known to a person skilled in the art such as crystallization from single solvent or combination of solvents by dissolving the compound optionally at elevated temperature and precipitating the compound by cooling the solution or removing solvent from the solution or both. It further includes methods such as solvent/antisolvent or precipitation.

The term "aryl" refers to an aromatic ring which contains from 3 to 12 carbon atoms. In one aspect the aromatic ring contains from 6 to 12 carbon atoms. Examples of aryl include phenyl, tropyl, indenyl, naphtyl, azulenyl, biphenyl and antracenyl. In one aspect, an example of aryl includes phenyl.

The term "alkyl" comprises linear or branched alkyl groups. Examples of alkyl include methyl, ethyl, n-propyl, iso-propyl, n-butyl, iso-butyl, tert-butyl, sec-butyl, pentyl, iso-pentyl, hexyl, heptyl, octyl, nonyl and decyl, and the isomers thereof.

The term "alkaryl" refers to an alkyl substituted with at least one aryl. Examples of alkaryls include benzyl and trityl.

The expression "polymorph form X essentially free of polymorph form Y" means that clevidipine butyrate polymorph form X prepared as disclosed herein contains less than about 1% of form Y as measured by XRD. By the expression "polymorph form X substantially free of polymorph form Y" means that the clevidipine butyrate polymorph form X prepared as disclosed herein contains less than about 15%, less than about 10%, or less than about 5-8% of form Y as measured by XRD.

DETAILED DESCRIPTION OF THE INVENTION

A first embodiment is directed to a process for the preparation of clevidipine butyrate in high purity and yields. Aspects of the disclosed process are described below.

A first aspect of the first embodiment is directed to a process comprising reacting compound I with methyl-3-Amino-crotonate, to obtain clevidipine butyrate in the presence of an organic solvent.

In a second aspect, the reacting occurs at a temperature below about 150° C.

In a third aspect, the reacting occurs at a temperature ranging from about 40° C. to about 150° C. and maintained for a sufficient time until the reaction is complete.

In a fourth aspect, the reacting occurs at a temperature ranging from about 10° C. below the refluxing temperature and refluxing temperature. In a sub-aspect the reacting occurs at a temperature ranging from about 5° C. below refluxing temperature and refluxing temperature.

In a fifth aspect, the mole ratio of compound I to methyl-3-Amino-crotonate is about one.

In a sixth aspect, the mole ratio of compound I to methyl-3-Amino-crotonate is one.

One of ordinary skill will appreciate that having a mole ratio of about one or one means advantageously that no substantial excess amount or excess amount of methyl-3-Amino-crotonate is needed.

In a seventh aspect, the organic solvent is an alcohol such as benzyl alcohol, 2-benzyloxyethanol, benzyl glycol, 1,10-decanediol, hexanediol, 1,2-butanediol, 1,3-butanediol, 1,4-butanediol, 2,3-butanediol, methanol, ethanol, isopropyl alcohol, n-propanol, tert-butanol, diethoxydiglycol, ethoxydiglycol, ethylene glycol, ethylene glycol mono-n-butyl ether, hexandiol, 1,2-hexanediol, 1,2,6-hexanetriol, hexylene glycol, isobutoxypropanol, isopentyldiol, 3-methoxybutanol, methoxybutanol, methoxyethanol, methoxyisopropanol, methoxymethylbutanol, pentylene glycol, 2-phenoxyethanol, 1-phenoxy-2-propanol, 2-phenyethanol, propanediol, propylene glycol, trimethyl-1,3-pentanediol; a ketone such as acetone, methyl ethyl ketone, methyl isobutyl ketone; an ether such as methyl tert-butyl ether; an ester such as methyl acetate, ethyl acetate, propyl acetate, isopropyl acetate, butyl acetate, isobutyl acetate; and a hydrocarbon such as toluene, methyl cyclohexane, xylene and mixtures thereof.

In an eighth aspect, the organic solvent is ethanol, isopropyl alcohol, or n-propyl alcohol.

In a ninth aspect, the organic solvent is isopropyl alcohol (IPA).

In a tenth aspect, clevidipine butyrate can be purified by standard purification and isolation methods using solvents such as water, an organic solvent or mixtures thereof. In a sub-aspect, an organic solvent includes but is not limited to an ether, such as diisopropyl ether (DIPE), methyl tert-butyl ether, diethyl ether; linear and cyclic hydrocarbons such as toluene, methyl cyclohexane, xylene, n-hexane; and a short chain alcohols such as methanol, ethanol, IPA, n-propanol and mixtures thereof. In a sub-aspect, the organic solvent is methyl cyclohexane.

Unexpectedly, it has been found that clevidipine butyrate is obtained in a high purity and yield.

An advantage of the fifth and sixth aspects where the mole ratio of compound I and methyl-3-Amino-crotonate is about one or one, is that no excess of methyl-3-Amino-crotonate is needed to be industrially feasible, which minimizes or eliminates the generation of impurities.

An additional advantage regarding the use of methyl-3-Amino-crotonate in the last step relates to the fact that the impurities similar to clevidipine butyrate are avoided. This aspect provides for an improved and a simplified separation of high purity clevidipine butyrate.

A further advantage is that the starting materials and co-reactants are non-toxic and they are either commercially available or may be obtained with fewer synthetic steps when compared with the processes disclosed in the art.

Additionally, unlike the known processes, the disclosed process is not restricted to any kind of solvent, which means that low toxic solvent can be used without losing process efficiency.

Another advantage is that a disclosed method permits isolation of some of the synthetic intermediates, which is a clear advantage, as it is explained below.

In an eleventh aspect, clevidipine butyrate can be further purified by using standard purification and isolation techniques such as, crystallization, washing or slurring with organic solvents, water or mixtures thereof. In a sub-aspect, suitable organic solvents include an alcohol such as benzyl alcohol, 2-benzyloxyethanol, benzyl glycol, 1,10-decanediol, hexanediol, 1,2-butanediol, 1,3-butanediol, 1,4-butanediol, 2,3-butanediol, methanol, ethanol, isopropyl alcohol, n-propanol, tert-butanol, diethoxydiglycol, ethoxydiglycol, ethylene glycol, ethylene glycol mono-n-butyl ether, hexandiol, 1,2-hexanediol, 1,2,6-hexanetriol, hexylene glycol, isobutoxypropanol, isopentyldiol, 3-methoxybutanol, methoxybutanol, methoxyethanol, methoxyisopropanol, methoxymethylbutanol, pentylene glycol, 2-phenoxyethanol, 1-phenoxy-2-propanol, 2-phenyethanol, propanediol, propylene glycol, trimethyl-1,3-pentanediol; an ether such as THF and diisopropylether (DIPE); a ketone such as, acetone, methyl ethyl ketone (MEK) and methyl isobutyl ketone (MIBK); and mixtures thereof. In a sub-aspect, purification is carried out using water, isopropanol, propanol, acetone, methanol, DIPE, and mixtures thereof.

A second and third embodiment is directed to a compound II, 2-(2',3'-Dichloro-benzylidene)-3-oxo-butyric acid and salts thereof as well as their use as intermediates for the preparation of clevidipine butyrate. Salts of compound II include salts of alkaline metal cations such as potassium and sodium salts. These intermediate compounds are obtained in high purity and yield and can be easily isolated and purified by using standard industrial methods, avoiding the use of column chromatography.

A fourth embodiment is directed to a method to prepare compound II or a salt thereof, comprising the hydrolysis of compound (III), wherein compound (III) is obtained by the reaction of compound (IV) and (V), as depicted in the scheme below,

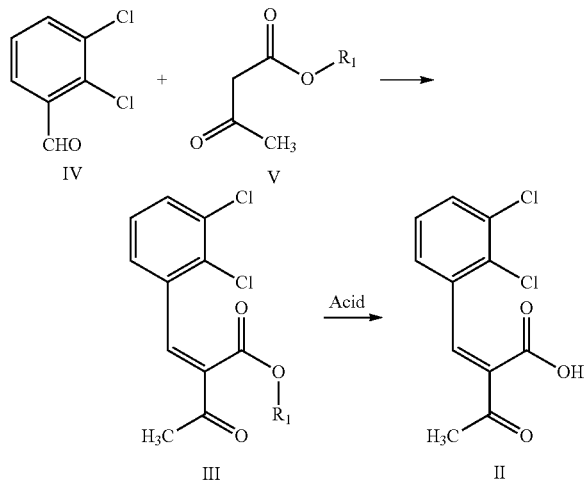

which comprises the steps of:
reacting compound IV (2,3-Dichloro-benzaldehyde) with a compound of formula V, $CH_3-CO-CH_2-COOR_1$, wherein $R_1$ is an alkyl, such as methyl, ethyl, propyl, isopropyl, butyl, tert-butyl; an aryl, such as a phenyl; or an alkaryl, such as benzyl and trityl, in the presence of an organic base and/or an acid to obtain compound III; and
hydrolyzing compound III in the presence of an acid, to obtain compound II or a salt thereof.

In a first aspect, the reacting occurs in the presence of an acid selected from acetic acid, formic acid, trifluoroacetic acid, sulfuric acid, hydrochloric acid, hydrobromic acid, and mixtures thereof.

In a second aspect, the reacting occurs in the presence of an organic base selected from a secondary linear amine, a tertiary linear amine, a secondary cyclic amine, and a tertiary cyclic amine.

In a third aspect, the reacting occurs in the presence of an organic base selected from piperidine, morpholine, triethyl amine, diisopropyl ethyl amine, and diethyl amine.

In a fourth aspect, the reacting occurs in the presence of an organic base selected from piperidine and morpholine.

In a fifth aspect, the reacting occurs in the presence of a basic salt.

In a sixth aspect, the reacting occurs in the presence of morpholine acetate.

In a seventh aspect, the hydrolyzing occurs in the presence of an organic acid or an inorganic acid.

In an eighth aspect, the hydrolyzing occurs in the presence of an organic acid selected from a carboxylic acid.

In a ninth aspect, the hydrolyzing occurs in the presence of an organic acid selected from formic acid, acetic acid, trifluoroacetic acid, oxalic acid, benzoic acid, and mixtures thereof.

In a tenth aspect the hydrolyzing occurs in the presence of formic acid.

In an eleventh aspect, the hydrolyzing occurs in the presence of an inorganic acid selected from HCl, HBr, $H_2SO_4$, and mixtures thereof.

In a twelfth aspect, the hydrolyzing occurs in the presence of sulfuric acid.

In a thirteenth aspect, the fourth embodiment further comprises purifying compound II by means of standard industrial purification and isolation methods.

In a fourteenth aspect, the fourth embodiment further comprises purifying compound II by washing with an organic solvent, in which the generated acid has low solubility. In a sub-aspect, the organic solvent is selected from toluene, hexane, methyl tert-butyl ether, methyl cyclohexane, xylene and mixtures thereof. In another sub-aspect, the organic solvent is toluene.

Compound II can be obtained as cis or trans isomer and mixtures thereof. The ratio of each isomer in the mixture is irrelevant to for their use as reactants in the next step (step b or condensation of compound II).

In a fifteenth aspect, the fourth embodiment further comprises adding an alkali metal base to compound II, followed by stirring for a period of time sufficient to form the alkali metal salt of compound II. In a sub-aspect, the alkali metal is potassium, sodium, or lithium.

In a sixteenth aspect, the fourth embodiment further comprises purifying compound II or salt thereof by standard industrial purification methods.

Fifth and sixth embodiments are directed to compound I, (2,3-Dichloro-benzylidene)-3-oxo-butyric acid butyryloxymethyl ester and process thereof as well as their use as intermediates for the preparation of clevidipine butyrate.

A seventh embodiment is directed to a process for preparing compound I

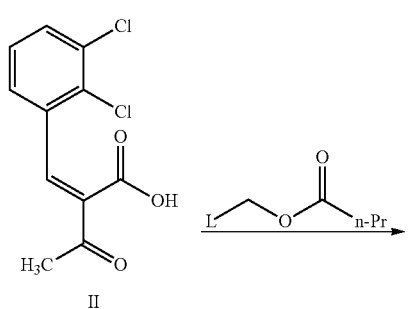

-continued

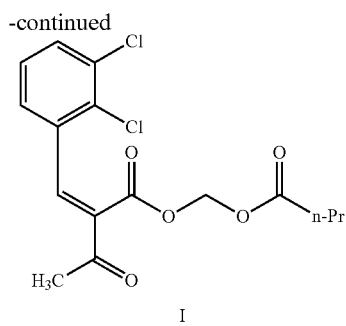

I by a method, which comprises:
condensing compound II or a salt thereof with a compound of formula L-CH$_2$OCO-n-Pr in the presence of a base and an organic solvent;
wherein L is a leaving group to obtain Compound I (2-(2',3'-Dichloro-benzylidene)-3-oxo-butyric acid butyryloxymethyl ester).

In a first aspect, the leaving group is a halogen or a sulfonyloxy group.

In a second aspect the leaving group is —OSO$_2$R$_2$ wherein R$_2$ is p-toluoyl, trifluoromethyl, fluorine, or alkyl.

In a third aspect the leaving group is —OSO$_2$CH$_3$.

In a fourth aspect the leaving group is Cl.

In a fifth aspect, the base is organic or inorganic.

In a sixth aspect, the base is an organic base.

In a seventh aspect, the base is an organic base selected from a secondary amine and a tertiary amine.

In an eighth aspect, the base is selected from triethyl amine, diisopropyl ethyl amine, and diethyl amine.

In a ninth aspect, the base is selected from triethyl amine and diisopropyl ethyl amine.

In a tenth aspect, the base is an inorganic base.

In an eleventh aspect the base is selected from ammonium hydroxide aqueous or alcoholic solution, sodium bicarbonate, sodium carbonate, potassium carbonate, and potassium bicarbonate.

In a twelfth aspect, the organic solvent is selected from an alcohol, an ester, a ketone, a cyclic hydrocarbon, and mixtures thereof.

In a thirteenth aspect, the organic solvent is selected from benzyl alcohol, 2-benzyloxyethanol, benzyl glycol, 1,10-decanediol, hexanediol, 1,2-butanediol, 1,3-butanediol, 1,4-butanediol, 2,3-butanediol, methanol, ethanol, isopropyl alcohol, n-propanol, tert-butanol, diethoxydiglycol, ethoxydiglycol, ethylene glycol, ethylene glycol mono-n-butyl ether, hexandiol, 1,2-hexanediol, 1,2,6-hexanetriol, hexylene glycol, isobutoxypropanol, isopentyldiol, 3-methoxybutanol, methoxybutanol, methoxyethanol methoxyisopropanol, methoxymethylbutanol, pentylene glycol, 2-phenoxyethanol, 1-phenoxy-2-propanol, 2-phenyethanol, propanediol, propylene glycol, trimethyl-1,3-pentanediol, acetone, methyl ethyl ketone, methyl tert butyl ether, ethyl acetate, methyl acetate, propyl acetate, isopropyl acetate, butyl acetate, isobutyl acetate, diisopropyl ether, dimethylacetamide, toluene, xylene, methyl cyclohexane, dichloromethane, and mixtures thereof.

In a fourteenth aspect, the organic solvent is selected from dichloromethane, acetone, methylethyl ketone, methyl isobutyl ketone, dimethylacetamide, toluene, xylene, methyl cyclohexane, methyl tert-butyl ether, THF, methyl acetate, ethyl acetate, propyl acetate, isopropyl acetate, butyl acetate, isobutyl acetate, and mixtures thereof.

In a fifteenth aspect, the organic solvent is selected from ethanol, isopropyl alcohol and n-propyl alcohol, diisopropyl ether, and mixtures thereof.

As noted above, Compound II can be obtained as a cis or a trans isomer and mixtures thereof. The ratio of each isomer in the mixture is irrelevant to for its use of compound II as a reactant in this step.

In a sixteenth aspect, the seventh embodiment further comprises condensing in the presence of a phase transfer catalyst.

In a seventeenth aspect, the seventh embodiment further comprises condensing in the presence of a phase transfer catalyst selected from tetrabutyl ammonium bromide, tetrabutyl ammonium chloride, tetrabutyl ammonium sulfate, and a polyethylene glycol.

In an eighteenth aspect, the seventh embodiment further comprises purifying compound I by standard industrial methods.

Compounds II and I are advantageously obtained in high purity and can be easily isolated and purified, as solids, by using standard industrial methods, avoiding the use of column chromatography which is a clear advantage.

An additional embodiment is directed to crystalline forms of clevidipine butyrate, useful to improve the pharmaceutical performance of pharmaceutical products, and methods for preparing thereof. There is a need in the art form new polymorphic forms of clevidipine butyrate and for their preparation as pure forms. The preparation methods herein described, allow the obtainment of polymorphs of clevidipine butyrate free of other polymorphic forms. Mixtures of polymorphic forms were also obtained as described in some of the experiments.

An eighth embodiment is directed to crystalline Form A of clevidipine butyrate.

In a first aspect, Form A of clevidipine butyrate has a m.p. (melting point) 138.8° C. (measured by DSC).

In a second aspect, Form A of clevidipine butyrate has substantially the same XRD pattern as that depicted in FIG. 1.

One of ordinary skill will appreciate that the an XRD pattern for each crystalline form is unique, exhibiting a unique set of diffraction peaks, which can be expressed in 2 theta angles (°), d-spacings (Å) and/or relative peak intensities. Large variations of relative peak intensities may be observed due to preferred orientation resulting from difference in crystal morphologies. Identification of the exact crystal form of a compound should be based primarily on the observed 2 theta angles or d-spacings with lesser importance focused on relative intensities.

In a third aspect, Form A of clevidipine butyrate has an XRD pattern expressed in terms of 2 theta angle, wherein the XRD pattern comprises 2 theta angles at four or more positions, selected from the group consisting of: 8.5±0.2, 16.2±0.2, 18.7±0.2, 22.2±0.2, 24.8±0.2, 25.4±0.2, 25.8±0.2, 27.7±0.2.

Although, one skilled in the art can identify form A of clevidipine butyrate from these peaks, in some circumstances it may be desirable to rely on additional 2 theta angles for the identification of form A of clevidipine butyrate.

In a fourth aspect, Form A of clevidipine butyrate has an XRD pattern expressed in terms of 2 theta angle, comprising 2 theta angles at four or more positions, selected from the group consisting of: 8.5±0.2, 16.2±0.2, 18.7±0.2, 22.2±0.2, 24.8±0.2, 25.4±0.2, 25.8±0.2, 27.7±0.2, and additional peaks at the following positions: 10.84±0.2, 14.35±0.2, 19.49±0.2, 21.2±0.2, 21.76±0.2, 24.07±0.2, 27.38±0.2, 28.0±0.2.

In a fifth aspect, Form A of clevidipine butyrate exhibits an XRD pattern that is substantially the same XRD pattern as that depicted in FIG. 1.

Figure 2:
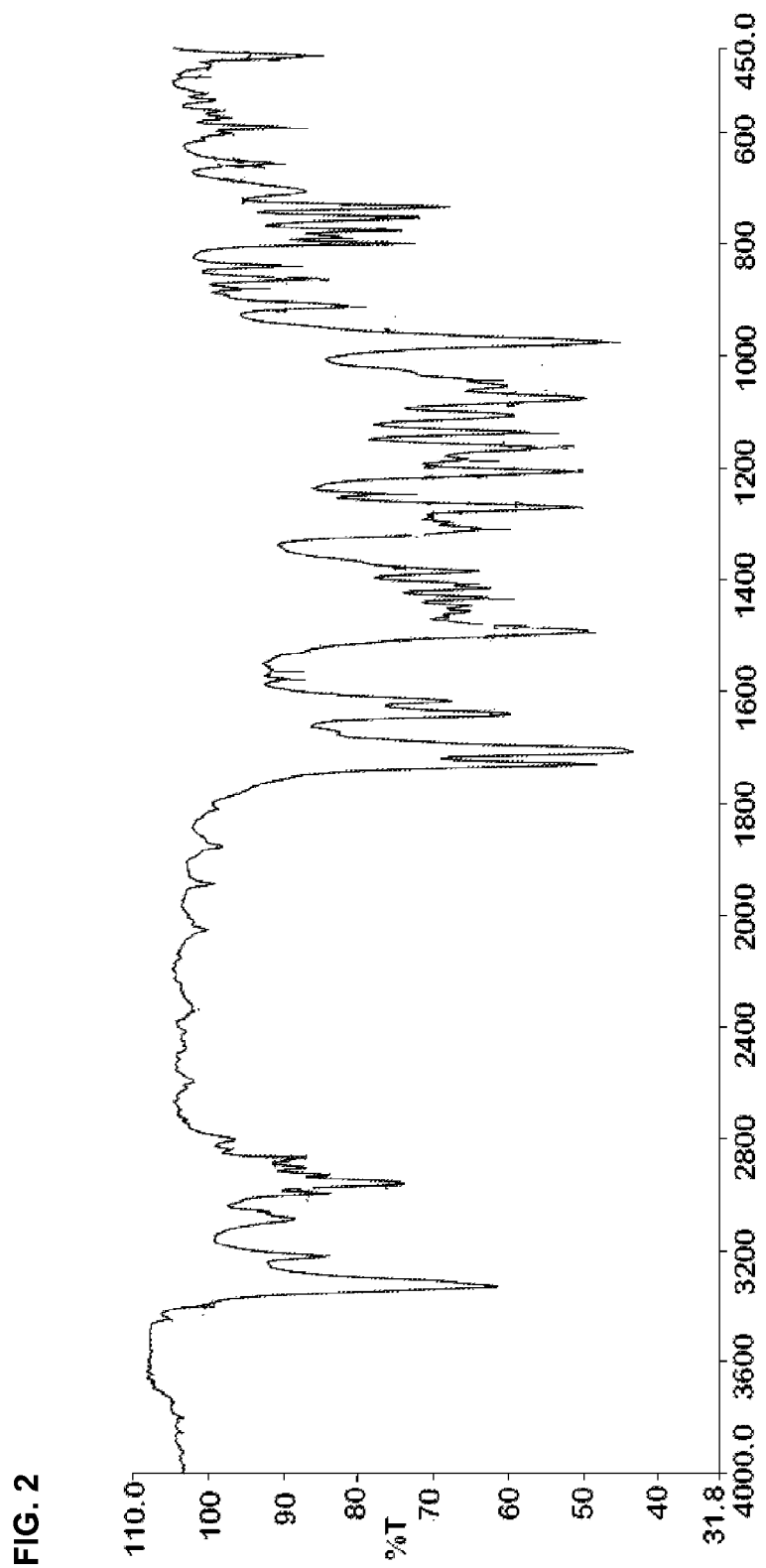
FIG. 2: FTIR of clevidipine butyrate form A.

In a sixth aspect, Form A of clevidipine butyrate exhibits an IR pattern that is substantially the same IR pattern as that depicted in FIG. 2.

A ninth embodiment is directed to a process for preparing polymorph A of clevidipine butyrate, which comprises:
  i) Dissolving clevidipine butyrate in an organic solvent at a temperature above about 65° C.;
  ii) Optionally, adding activated charcoal at about room temperature for half and hour and removing the charcoal from the media;
  iii) Adding water to the clevidipine butyrate solution at about room temperature and stirred the mixture until a precipitate is obtained; and
  iv) Removing clevidipine butyrate from the medium.

An advantage of the eighth embodiment is that polymorph A of clevidipine butyrate can be obtained that is essentially free of other polymorphic forms.

A tenth embodiment is directed to crystalline from B of clevidipine butyrate.

In a first aspect, Form B of clevidipine butyrate has a melting point (m.p.) of 142.8° C. (measured by DSC).

Figure 3:
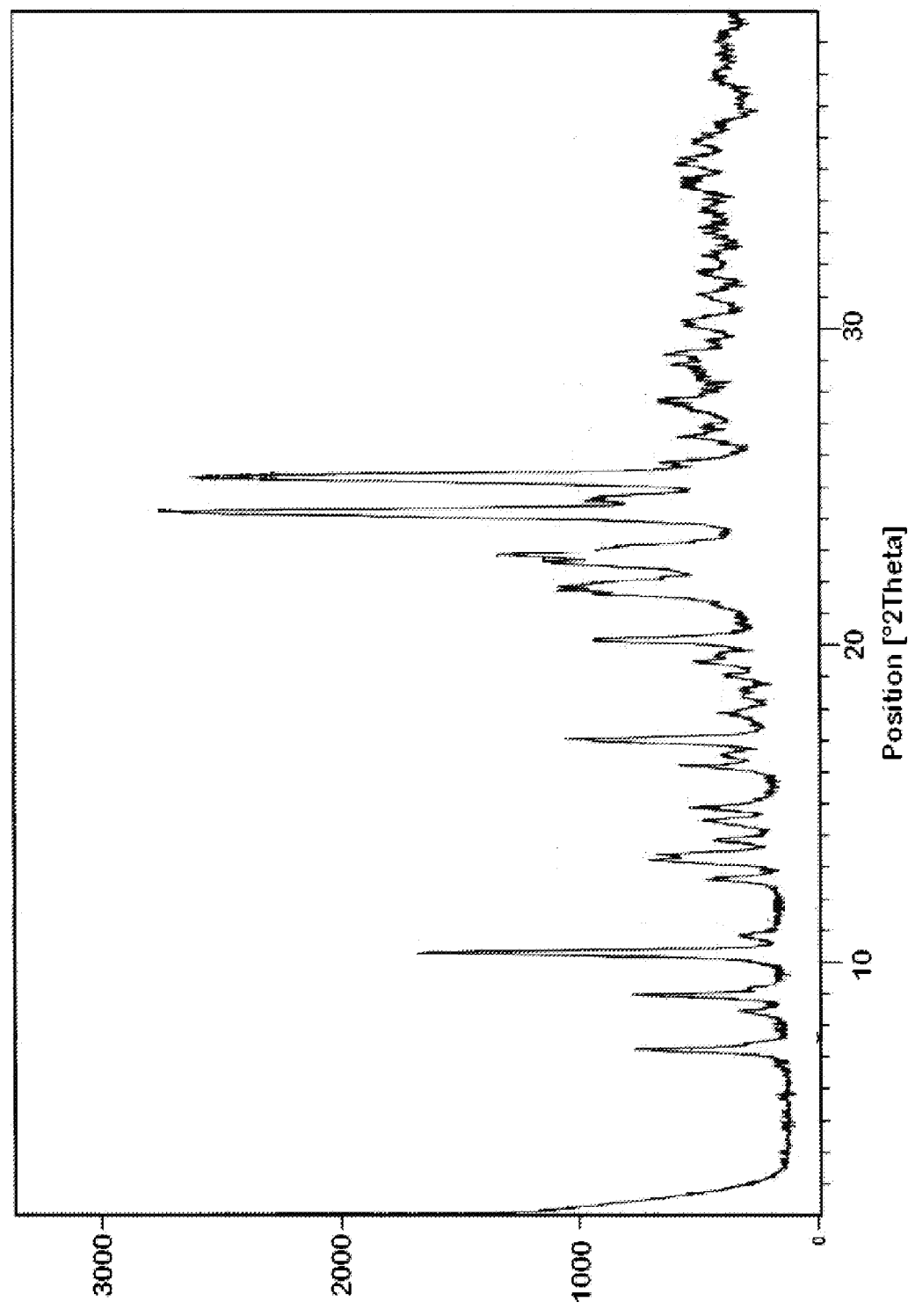
FIG. 3: XRD of clevidipine butyrate form B.

In a second aspect Form B of clevidipine butyrate has substantially the same XRD pattern as that depicted in FIG. 3.

In a third aspect, Form B of clevidipine butyrate has an XRD pattern expressed in terms of 2 theta angle, wherein the XRD pattern comprises 2 theta angles at four or more positions selected from the group consisting of XRD: 7.24±0.2, 8.95±0.2, 10.29±0.2, 17.02±0.2, 20.21±0.2, 21.87±0.2, 22.57±0.2, 22.87±0.2, 24.23±0.2, 25.39±0.2.

In a fourth aspect, Form B of clevidipine butyrate exhibits an XRD pattern expressed in terms of 2 theta angle, wherein the XRD pattern comprises 2 theta angles at four or more positions selected from the group consisting of XRD: 7.24±0.2, 8.95±0.2, 10.29±0.2, 17.02±0.2, 20.21±0.2, 21.87±0.2, 22.57±0.2, 22.87±0.2, 24.23±0.2, 25.39±0.2 and additional peaks at essentially the following positions: 13.22±0.2, 13.39±0.2, 16.19±0.2, 23.12±0.2, 24.66±0.2.

In a fifth aspect, Form B of clevidipine butyrate has substantially the same XRD pattern as that depicted in FIG. 3.

Figure 4:
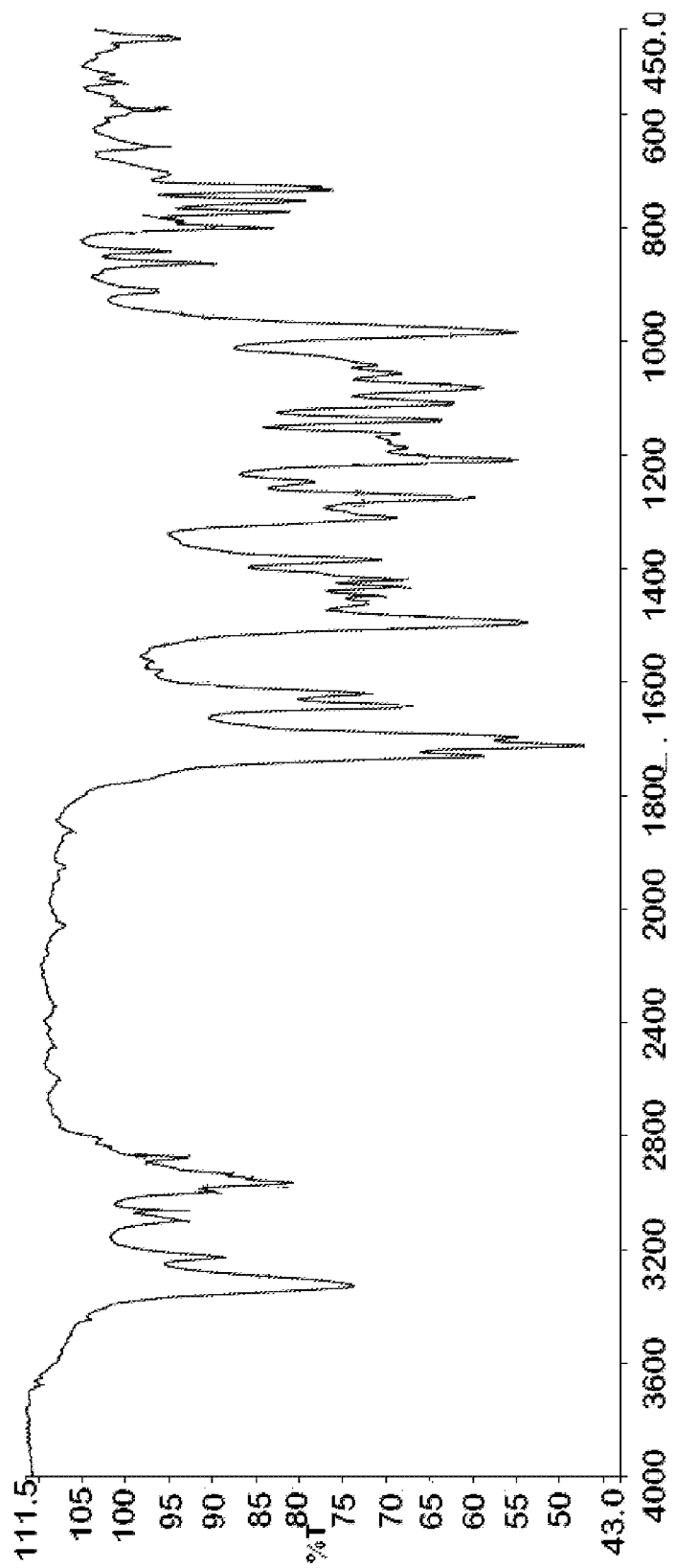
FIG. 4: FTIR of clevidipine butyrate form B.

In a sixth aspect, Form B of clevidipine butyrate has an IR pattern substantially the same IR pattern as that depicted in FIG. 4.

An eleventh embodiment is directed to a process for the preparation of polymorph B of clevidipine butyrate, which comprises:
  i) Dissolving clevidipine butyrate in an organic solvent;
  ii) Adding water at about room temperature and stirring the mixture until a precipitate is obtained; and
  iii) Removing clevidipine butyrate from the medium.

An advantage of the tenth embodiment provides for the preparation of polymorph B of clevidipine butyrate essentially free of other polymorphic forms.

Additional embodiments are directed to a pharmaceutical composition of clevidipine butyrate comprising any one of the polymorphs described herein and their use for the reduction of blood pressure when oral therapy is not feasible or not desirable.

Additional embodiments are also directed to a pharmaceutical composition of clevidipine butyrate prepared by any one of the methods described herein and their use for the reduction of blood pressure when oral therapy is not feasible or not desirable.

Additional embodiments are further directed to the use of compounds II and III for the preparation of clevidipine butyrate.

The inventors have developed formulations comprising polymorph forms A and/or B of clevidipine butyrate with excellent properties as pharmaceutical products.

Additional embodiments are described in the following clauses below:

Clause 1. A process for the preparation of clevidipine butyrate comprising the step:
(i) reacting a compound of formula (I):

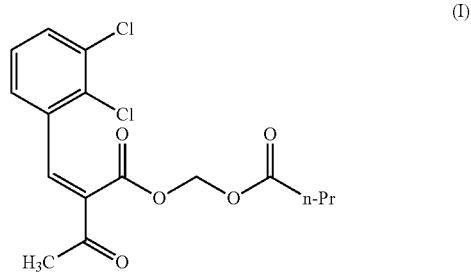

with methyl 3-amino crotonate to obtain clevidipine butyrate, wherein the step (i) is carried out in the presence of at least an organic solvent or a solvent mixture comprising an organic solvent.

Clause 2. The process according to clause 1, wherein the mole ratio of methyl 3-aminocrotonate to compound of formula (I) ranges from about 2:1 to 1:2, from about 1.25:1 to 1:1.25, or about 1:1.

Clause 3. The process according to any one of the preceding clauses, wherein the step (i) is carried out at a temperature below about 150° C.

Clause 4. The process according to the preceding clause, wherein the step (i) is carried out at a temperature ranging from about 50° C. to about 120° C.

Clause 5. The process according to any one of the preceding clauses, comprising an organic solvent selected from benzyl alcohol, 2-benzyloxyethanol, benzyl glycol, 1,10-decanediol, hexanediol, 1,2-butanediol, 1,3-butanediol, 1,4-butanediol, 2,3-butanediol, methanol, ethanol, isopropyl alcohol, n-propanol, tert-butanol, diethoxydiglycol, ethoxydiglycol, ethylene glycol, ethylene glycol mono-n-butyl ether, hexandiol, 1,2-hexanediol, 1,2,6-hexanetriol, hexylene glycol, isobutoxypropanol, isopentyldiol, 3-methoxybutanol, methoxybutanol, methoxyethanol, methoxyisopropanol, methoxymethylbutanol, pentylene glycol, 2-phenoxyethanol, 1-phenoxy-2-propanol, 2-phenyethanol, propanediol, propylene glycol, trimethyl-1,3-pentanediol, acetone, methyl ethyl ketone, methyl tert butyl ether, ethyl acetate, methyl acetate, propyl acetate, isopropyl acetate, butyl acetate, isobutyl acetate, diisopropyl ether toluene, methyl cyclohexane, xylene, and mixtures thereof.

Clause 6. The process according to any one of the preceding clauses, wherein the organic solvent is selected from methanol, ethanol, isopropyl alcohol, n-propanol, tert-butanol, acetone, methyl ethyl ketone, methyl tert butyl ether, ethyl acetate, methyl acetate, propyl acetate, isopropyl acetate, butyl acetate, isobutyl acetate, diisopropyl ether toluene, methyl cyclohexane, xylene, and mixtures thereof.

Clause 7. The process according to the preceding clause, wherein the organic solvent is selected from ethanol, isopropyl alcohol and n-propyl alcohol, diisopropyl ether, and mixtures thereof.

Clause 8. The process according to any one of the preceding clauses, wherein the compound of formula (I) is prepared by esterifying a compound of formula (II) or a salt thereof:

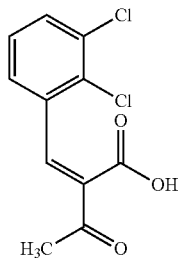

(II)

with a compound of formula L-CH$_2$OCO-n-Pr, wherein L is a leaving group.

Clause 9. The process according to preceding clause, wherein the esterifying occurs in the presence of at least one organic and/or inorganic base.

Clause 10. The process according to the preceding clause, wherein the base is selected from a secondary amine, a tertiary amine, an ammonium hydroxide solution, an alkali metal carbonate, an alkaline earth metal carbonate, an alkali metal bicarbonate, an alkaline earth metal bicarbonate, and mixtures thereof.

Clause 11. The process according to the preceding clause, wherein the base is selected from triethyl amine, diisopropyl ethyl amine, an ammonium hydroxide solution, sodium bicarbonate, sodium carbonate, potassium carbonate, potassium bicarbonate, and mixtures thereof.

Clause 12. The process according to any one of the clauses 8 to 11, wherein the leaving group is selected from a carboxyl ester, a halogen, and a sulfonyloxy groups represented by —OSO$_2$R$_2$, wherein the R$_2$ is an alkyl, p-toluoyl, trifluoromethyl, or fluorine.

Clause 13. The process according to the preceding clause, wherein the leaving group is selected from trifluoromethylsulfonyl, para-nitrobenzenesulfonyl, para-toluenesulfonyl, methylsulfonyl, trifluoroacetyl, para-nitrobenzoyl, para-methylbenzoyl, acetyl, iodine, bromine, chlorine, and fluorine.

Clause 14. The process according to the preceding clause, wherein the leaving group is chlorine.

Clause 15. The process according to any one of the clauses 8 to 14, wherein the esterifying occurs in the presence of an organic solvent selected from dichloromethane, a ketone, a cyclic hydrocarbon, a linear ether, a cyclic ether, an ester, and mixtures thereof.

Clause 16. The process according to any one of the clauses 8 to 14, wherein the esterifying occurs in the presence of dichloromethane, acetone, methylethyl ketone, methyl isobutyl ketone, dimethylacetamide, toluene, xylene, methyl cyclohexane, methyl tert-butyl ether, THF, methyl acetate, ethyl acetate propyl acetate, isopropyl acetate, butyl acetate, isobutyl acetate, and mixtures thereof.

Clause 17. The process according to preceding clause, wherein the esterifying occurs in the presence of phase transfer catalysts.

Clause 18. The process according to the preceding clause, wherein the esterifying occurs in the presence of tetrabutyl ammonium bromide, tetrabutyl ammonium chloride, tetrabutyl ammonium sulfate, polyethylene glycol, and mixtures thereof.

Clause 19. The process according to any one of the clauses 8 to 18, wherein the compound of formula (II) is obtained by hydrolyzing of the compound of formula (III), wherein R$_1$ is selected from: an alkyl, such as methyl, ethyl, propyl, isopropyl, butyl and tert-butyl; an aryl, such as phenyl; or an alkaryl, such as benzyl and trityl.

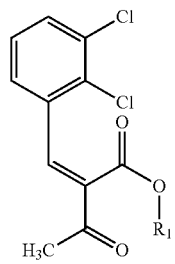

(III)

Clause 20. The process according to any one of the clauses 8 to 18, wherein R$_1$ is selected from methyl, ethyl, propyl, isopropyl, butyl, tert-butyl, phenyl, benzyl, and trityl.

Clause 21 The process according to any one of clauses 19 and 20, wherein the hydrolyzing occurs in the presence of an acid or a base.

Clause 22. The process according to the preceding clause, wherein the hydrolyzing occurs in the presence of an acid.

Clause 23. The process according to the preceding clause, wherein the acid is selected from hydrogen halides and their solutions; halogen oxoacids; sulfuric acid (H$_2$SO$_4$); nitric acid (HNO$_3$); phosphoric acid (H$_3$PO$_4$); fluoroboric acid; sulfonic acids; carboxylic acids; and mixtures thereof.

Clause 24. The process according to the preceding clause, wherein the acid is selected from hydrochloric acid (HCl), hydrobromic acid (HBr), hydroiodic acid (HI); hypochloric acid (HClO), chloric acid (HClO$_3$), perchloric acid (HClO$_4$), hypobromous acid (HBrO), bromic acid (HBrO$_3$), perbromic acid (HBrO$_4$), hyopiodous acid (HIO), iodic acid (HIO$_3$), periodic acid (HIO$_4$), sulfuric acid (H$_2$SO$_4$), nitric acid (HNO$_3$), phosphoric acid (H$_3$PO$_4$), fluoroboric acid, methanesulfonic acid (CH$_3$SO$_3$H), ethanesulfonic acid (CH$_3$CH$_2$SO$_3$H), benzenesulfonic acid (C$_6$H$_5$SO$_3$H), p-toluenesulfonic acid (CH$_3$C$_6$H$_4$SO$_3$H), trifluoromethanesulfonic acid (CF$_3$SO$_3$H), acetic acid, trifluoroacetic, citric acid, formic acid, gluconic acid, lactic acid, oxalic acid, tartaric acid, succinic acid, malic acid, and mixtures thereof.

Clause 25. The process according to the preceding clause, wherein the acid is selected from trifluoroacetic acid, sulfuric acid, hydrochloric acid, hydrobromic acid, formic acid, trifluoroacetic acid, and mixtures thereof.

Clause 26. The process according to the preceding clause, wherein the acid is selected from formic acid, trifluoroacetic acid, and mixtures thereof.

Clause 27. The process according to the clause 24, wherein the acid is selected from sulfuric acid, hydrochloric acid, hydrobromic acid, and mixtures thereof.

Clause 28. The process according to any one of the clauses 19 to 27, wherein the compound of formula (III) is obtained by reacting compound of formula (IV) (2,3-dichloro-benzaldehyde) with a compound of formula (V) (CH$_3$—CO—C$_2$—COOR$_1$):

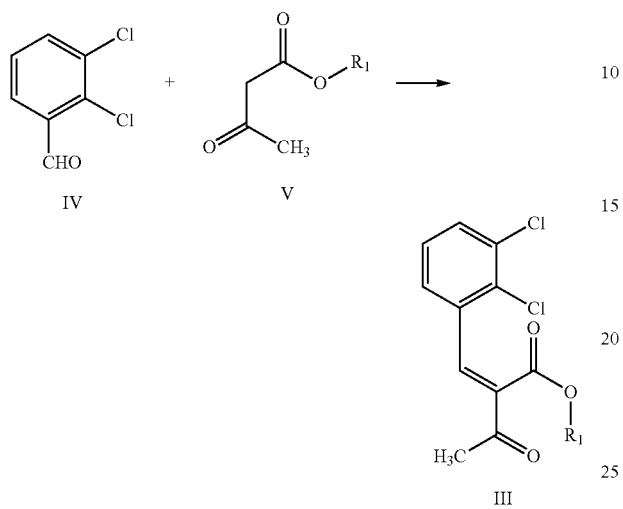

wherein R$_1$ is as defined above in the Clause 19.

Clause 29. The process according to the preceding clauses, wherein the reacting occurs in the presence of a base and/or an acid.

Clause 30. The process according to the preceding clauses, wherein the acid is selected from acetic acid, formic acid, trifluoroacetic acid, sulfuric acid, hydrochloric acid, hydrobromic acid, and mixtures thereof; and the base is selected from a secondary linear amine, a secondary cyclic amine, a tertiary linear amine, and a tertiary cyclic amines.

Clause 31. The process according to the preceding clauses, wherein the acid is selected from acetic acid, formic acid, trifluoroacetic acid, sulfuric acid, hydrochloric acid, hydrobromic acid; and mixtures thereof; and the base is selected from piperidine, morpholine, triethyl amine, diisopropyl ethyl amine, diethyl amine, and mixtures thereof.

Clause 32. The process according to the preceding clause, wherein the base is selected from piperidine, morpholine, and mixtures thereof.

Clause 33. The process according to clauses 28 and 29, wherein the reacting occurs in the presence of a basic salt.

Clause 34. The process according to the preceding clause, wherein the basic salt is morpholine acetate.

Clause 35. The process according to any one of the preceding clauses, further comprising purifying the clevidipine butyrate obtained in the step (i).

Clause 36. The process according to the preceding clause, wherein the clevidipine butyrate is at least purified by a method selected from solvent extraction, filtration, slurring, washing, phase separation, evaporation, centrifugation, crystallization, and combinations thereof.

Clause 37. The process according to the preceding clause, wherein the clevidipine butyrate is at least purified by a method selected from slurring, washing, crystallization, and combinations thereof.

Clause 38. A compound of formula (I):

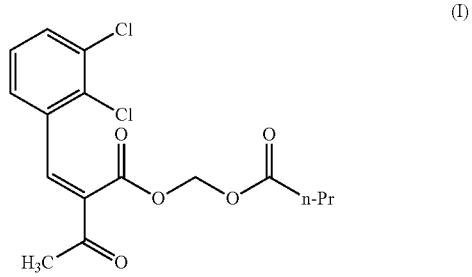

Clause 39. A compound of formula (II) or a salt thereof:

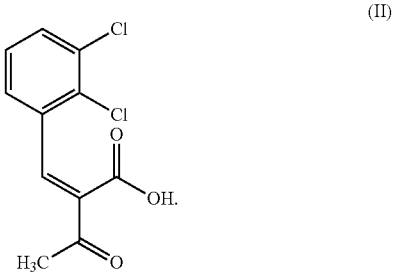 [SMILES: CC(=O)/C(=C/c1cccc(Cl)c1Cl)C(=O)O]

Clause 40. A crystalline polymorph clevidipine butyrate form A that exhibits an X-ray powder diffraction pattern having characteristic peaks expressed in degrees 2-theta at approximately 8.5±0.2, 16.2±0.2, 18.7±0.2, 22.1±0.2, 24.8±0.2, 25.4±0.2, 25.8±0.2, 27.7±0.2.

Clause 41. The crystalline polymorph form A of clevidipine butyrate according to preceding clause which is substantially free of the form B polymorph.

Clause 42. The crystalline polymorph form A of clevidipine butyrate according to the preceding clauses which is essentially free of the clevidipine butyrate form B polymorph.

Clause 43. The crystalline polymorph form A of clevidipine butyrate according to any one of the clauses 40 to 42, characterized by the X-ray powder diffraction pattern substantially as shown in FIG. 1.

Clause 44. The crystalline polymorph form A of clevidipine butyrate according to any one of the clauses 40 to 43 which is characterized by an IR absorption spectrum having characteristic peaks expressed in cm$^{-1}$ at approximately 3333±1, 3225±1, 2967±1, 1732±1, 1710±1, 1641±1, 1493±1, 1272±1, 1208±1, 1138±1, 1077±1, 976±1, 735±1, 464±1.

Clause 45. The crystalline polymorph form A of clevidipine butyrate of clause 44, characterized by the IR absorption spectrum substantially as shown in FIG. 2.

Clause 46. A pharmaceutical composition comprising any one of the polymorphs as defined in the clauses 40 to 45.

Clause 47. The pharmaceutical composition according to the preceding clause in the form of emulsion for injection.

Clause 48. The pharmaceutical composition according to the preceding clause in the form of lipid emulsion.

Clause 49. The pharmaceutical composition according to any of the clauses 38 to 40, wherein the concentration of clevidipine butyrate is about 0.5 mg/mL.

Clause 50. A crystalline polymorph clevidipine butyrate form B that exhibits an X-ray powder diffraction pattern having characteristic peaks expressed in degrees 2-theta at approximately 7.2±0.2, 9.0±0.2, 10.3±0.2, 17.0±0.2, 20.2±0.2, 21.9±0.2, 22.6±0.2, 22.9±0.2, 24.2±0.2, 25.4±0.2.

Clause 51. The crystalline polymorph form B of clevidipine butyrate according to preceding clause which is substantially free of the form A polymorph.

Clause 52. The crystalline polymorph form B of clevidipine butyrate according to the preceding clauses which is essentially free of the clevidipine butyrate form A polymorph.

Clause 53. The crystalline polymorph form B of clevidipine butyrate according to any one of the clauses 42 to 44, characterized by the X-ray powder diffraction pattern substantially as shown in FIG. 3.

Clause 54. The crystalline polymorph form B of clevidipine butyrate according to any one of the clauses 42 to 45 which is characterized by an IR absorption spectrum having characteristic peaks expressed in $cm^{-1}$ at approximately 3330±1, 3097±1, 2965±1, 1731±1, 1712±1, 1697±1, 1643±1, 1620±1, 1419±1, 1496±1, 1432±1, 1274±1, 1209±1, 1109±1, 1082±1, 984±1, 734.5±1, 728±1, 468±1.

Clause 55. The crystalline polymorph form B of clevidipine butyrate of clause 54, characterized by the IR absorption spectrum shown in FIG. 4.

Clause 56. A pharmaceutical composition comprising any one of the polymorphs as defined in the clauses 40 to 45 or 50 to 55.

Clause 57. The pharmaceutical composition according to the preceding clause in the form of emulsion for injection.

Clause 58. The pharmaceutical composition according to the preceding clause in the form of lipid emulsion.

Clause 59. The pharmaceutical composition according to any of the clauses 56 to 58, wherein the concentration of clevidipine butyrate is about 0.5 mg/mL.

Clause 60. The pharmaceutical composition according to the preceding clauses comprising soybean oil, optionally in an amount ranging from about 150 to about 250 mg/mL.

Clause 61. The pharmaceutical composition according to any of the clauses 59 to 60, comprising glycerine, optionally in an amount ranging from about 17 to about 27 mg/mL.

Clause 62. The pharmaceutical composition according to any of the clauses 51 to 53, comprising phospholipids, optionally purified egg yolk phospholipids, and also optionally in an amount ranging from about 17 to about 27 mg/mL.

Clause 63. The pharmaceutical composition according to any of the claims 59 to 62, wherein the composition has a pH ranging from about 5.9 to about 8.1.

Clause 64. A process for the preparation of polymorph form A of clevidipine butyrate according to clauses 40 to 45, which comprises:
  i) Dissolving clevidipine butyrate in an organic solvent at a temperature above about 65° C.;
  ii) Optionally, adding activated charcoal at about room temperature for half and hour and removing the charcoal from the media;
  iii) Adding water to the clevidipine solution at about room temperature and stirred the mixture until a precipitate is obtained; and
  iv) Removing clevidipine butyrate from the medium.

Clause 65. The process for the preparation of polymorph form A of clevidipine butyrate according to clause 64, wherein the organic solvent is selected from acetone, diethyl ketone, isopropanol, toluene, and mixtures thereof.

Clause 66. The process for the preparation of polymorph form A of clevidipine butyrate according any of the clauses 64 or 65 in which the dissolution step (i) takes place between about room temperature and about 120° C.

Clause 67. A process for the preparation of polymorph form B of clevidipine butyrate according to clause 50 to 55, which comprises:
  i) Dissolving clevidipine butyrate in an organic solvent;
  ii) Adding water at about room temperature and stirring the mixture until a precipitate is obtained; and
  iii) Removing clevidipine butyrate from the medium.

Clause 68. The process for the preparation of polymorph form B of clevidipine butyrate according to clause 67 wherein the organic solvent is selected from diisopropyl ether, an aqueous solution of methanol, and a combination thereof.

EXAMPLES

Not to be limited by way of example, the following examples serve to facilitate a better understanding of the claimed invention.

Reported melting points were measured using a Jade DSC by Perkin Elmer.

XRD diffractograms were obtained using a XPERT PRO by PANalytical.

FTIR spectra were obtained using a Spectrum 100 by Perkin Elmer.

Example 1

Preparation of benzylidine tert-butyl ester (Compound III)

50 g (0.285 mol) of 2,3-dichlorobenzaldehyde, 54.17 g (0.342 mol) tert-butyl 3-oxobutanoate, 1.45 g (0.017 mol) of piperidine, 200 ml isopropanol and 1.02 g (0.017 mol) acetic acid were charged in a one liter flask fitted with a reflux condenser. The reaction mass was heated up to 50° C. and stirred for 1 hour. Afterwards, the mixture was cooled down to 25-30° C. and stirred for 15 hours. The mixture was further cooled to 10-15° C. and stirred for 2 hours. The reaction mass was filtered and washed with 25 ml of chilled isopropanol and 50 ml of hexane. The white coloured solid was dried under reduced pressure at 50-55° C. for 7-8 hours. Yield: 70 g, Molar yield: 77.78%, HPLC purity: 98-99% and m.p.: 94 to 96° C.

Example 2

Preparation of benzylidine acid (2-acetyl-3-(2',3'-dichlorophenyl) prop-2-enoic acid) (Compound II)

70 g (0.222 mol) of benzylidine tert-butyl ester and 420 ml of formic acid (98-100%) were charged in a one liter flask fitted with reflux condenser and heated up to 50° C. The reaction mass was stirred for half an hour, followed by cooling and stirring at 25-30° C. for 7-8 hours. Formic acid was removed by distillation under reduced pressure at 45-50° C. Afterwards, 140 ml of toluene were charged and distilled out under vacuum at 50° C. Additional 140 ml of toluene were charged and stirred at 25-30° C. for 2 hours. The reaction mass was filtered and the precipitate dried at 50-55° C. for 8-10 hours. Yield: 48 g, Molar yield: 83.4%, White coloured solid, HPLC purity: 99.68% (Mixture of cis and trans isomers are present in a ratio of 61.79 and 38.02% respectively).

IR ($cm^{-1}$): 2931.2, 2625.58, 2540.8, 1733.6, 1623.2, 1675, 1450, 1411.3, 1363.4, 1285.7, 1274.5, 1235.5, 1182.8, 1166, 1049, 917, 898, 821, 796, 715, 656, 601, 567, 542.6, 459.7.

Example 3

Preparation of benzylidine Acid (2-acetyl-3-(2',3'-dichlorophenyl) prop-2-enoic acid) (Compound II)

50 g (0.158 mol) of benzylidine tert-butyl ester and 173 ml of sulfuric acid (50% v/v) were charged in a 0.25 liter flask and stirred for 7-8 hours at 25-30° C. The reaction mass was filtered and washed with 100 ml water. The obtained wet cake (35 gm) was stirred in 100 ml toluene at 25-30° C. for 1 hour. The solid was filtered and the product dried at 50-55° C. for 8-10 hours. A white solid obtained. Yield: 32.8 g, Molar yield: 80.15%, HPLC purity: 98.85% (Mixture of cis and trans isomers in the ratio of 39.93 and 60.06% respectively).

Example 4

Preparation of Benzylidine butyrate (2-(2',3'-Dichloro-benzylidene)-3-oxo-butyric acid butyryloxymethyl ester) (Compound I)

45 g (0.173 mol) of benzylidine acid, 28.95 g (0.286 mol) of triethyl amine and 450 ml dichloromethane were charged in a one liter flask fitted with a reflux condenser. Afterwards, 35.5 g (0.260 mol) of chloromethyl butyrate were slowly added at 25-30° C. under nitrogen atmosphere. The reaction mass stirred while heated at 40-45° C. for 30-35 hours. The obtained mixture was cooled down to 30° C. and washed twice with 200 ml of demineralised water (DM). The organic layer was separated and the dichloromethane distilled out under reduced pressure at 40-50° C. to obtain a yellowish coloured liquid.

Yield: 64 g, Molar yield: 103%, HPLC purity: 92.74% (Mixture of cis and trans isomers are present in a ratio of 62.90 and 37.09% respectively).

IR (cm$^{-1}$): 2968.2, 2936.2, 28877.3, 1761.6, 1703.2, 1678.2, 1625.5, 1558.8, 1452, 1412, 1377, 1363, 1273, 1237.7, 1183, 1158, 1140.4, 1105, 1050, 999, 980, 787, 717, 473, 457.

Example 5

Preparation of Potassium Salt of Benzylidine Acid 2.54 g (0.038 mol) of 85% potassium hydroxide and 150 ml isopropanol were charged in a 250 ml flask. The mixture was stirred at 50-55° C. for 30 minutes followed by cooling, down to 25° C. 10 g (0.038 mol) of benzylidine acid (compound II) were added into the flask and the mixture stirred at 20-25° C. for 1 hour. The formed solid was filtered and washed with 10 ml of isopropanol. The wet cake was dried under reduced pressure at 50-55° C. yielding 8.5 g of a white solid. Molar yield: 75.33%, HPLC purity: 99.7% (Mixture of cis and trans isomers in the ratio of 85.86 and 14.14% respectively).

Example 6

Preparation of Sodium Salt of Benzylidine Acid 1.54 g (0.038 mol) of sodium hydroxide and 150 ml isopropanol were charged in a 250 ml flask. The mixture was stirred at 50-55° C. for 30 minutes followed by cooling, down to 25° C. 10 g (0.038 mol) of benzylidine acid (compound II) were added into the flask and the mixture stirred at 20-25° C. for 1 hour. The formed solid was filtered and washed with 10 ml of isopropanol. The wet cake was dried under reduced pressure at 50-55° C. yielding 8.8 g of a white solid. Molar yield: 82.4%, HPLC purity: 99.8% (Mixture of cis and trans isomers in the ratio of 97.9 and 2.1% respectively).

Example 7

Preparation of Benzylidine butyrate (2-(2',3'-Dichloro-benzylidene)-3-oxo-butyric acid butyryloxymethyl ester) (Compound I)

5.0 g (0.0193 mol) of benzylidine acid, 2.92 g (0.0289 mol) of triethyl amine and 50 ml acetone were charged in a 250 ml flask fitted with a reflux condenser. 3.55 g (0.026 mol) of chloromethyl butyrate were slowly added at 25-30° C. under nitrogen atmosphere. The reaction mass was stirred at 55-58° C. for 15-20 hours, followed by cooling, down to 30° C., and filtering of the inorganic salts. Acetone was distilled out under reduce pressure at 45-50° C. The obtained mixture was diluted with 100 ml of ethyl acetate and washed with 100 ml of demineralized (DM) water twice. The organic layer was separated and the ethyl acetate distilled out under reduced pressure at 45-50° C. to yield a yellowish coloured liquid.

Yield: 6.5 g, Molar yield: 93.8%, HPLC purity: 91.58% (Mixture of cis and trans isomers are present in ratio of 64.91 and 35.09% respectively).

Example 8

Preparation of Benzylidine butyrate (2-(2',3'-Dichloro-benzylidene)-3-oxo-butyric acid butyryloxymethyl ester) (Compound I)

2.0 g (0.0067 mol) of potassium salt of benzylidine acid, 20 ml of dichloromethane and 0.4 g (0.004 mol) of triethyl amine were charged in a 100 ml flas. 1.37 g (0.010 moles) of chlomethyl butyrate were slowly added at 25-30° C. under nitrogen atmosphere. The reaction mass was stirred at 40-42° C. for 25-30 hours. Afterwards, the mixture was cooled down to 25° C. and washed twice with 25 ml of water. The organic and the aqueous layer were separated and the dichloromethane distilled out at 40-42° C. under reduced pressure. 2.2 g of a yellow coloured liquid were obtained. Molar yield: 91.46%, HPLC purity: 91.9% (Mixture of cis and trans isomers in the ratio of 60.94 and 39.06% respectively).

Example 9

Preparation of Crude Clevidipine Butyrate 60 g (0.167 mol) of benzylidine butyrate, 19.22 g (0.167 mol) methyl 3-amino crotonate and 300 ml isopropanol, were charged in 250 ml flask fitted with condenser. The reaction mass was stirred for 8-10 hours at reflux (80-82° C.) followed by cooling at 40° C. Afterwards, 300 ml DM water were slowly added to the reaction mass and stirred for 3 hours at 25-30° C. Filtered the reaction mass. The solid was washed with a 25 ml of a 50% isopropanol:water solution (v/v) to obtain 100 g of wet cake. The wet cake was suspended in 100 ml of methyl cyclohexane and heated up to 100° C. for 1 hour, followed by cooling and stirring at 25° C. for 2 hours. The product was filtered and washed with 25 ml methyl cyclohexane. A light yellow-coloured crude clevidipine butyrate was obtained after vacuum drying for 8-10 hours. Yield: 50.2 g, molar yield: 65.9% HPLC purity: 99.2%.

Example 10

Preparation of Clevidipine Butyrate 5.0 g (0.0139 mol) of benzylidine butyrate, 1.6 g (0.139 mol) methyl 3-amino crotonate and 25 ml diisopropyl ether were charged in a 100 ml flask fitted with condenser. The reaction mass was stirred for 8-10 hours at reflux (70° C.). Afterwards, the reaction mass was cool to 20-25° C. and stirred for 3 hours. The solid was filtered, washed with 20 ml of diisopropyl ether and dried under reduced pressure for 8-10 hours yielding 4.25 g of a light yellow coloured clevidipine butyrate (LOD<1.0%). Molar yield: 67%, HPLC purity: 98.98%.

m.p. by DSC: 142.1° C.

Clevidipine butyrate form B

Recrystallization from diisopropyl ether yields the same polymorphic form, clevidipine butyrate form B.

Example 11

Purification of Crude Clevidipine Butyrate 10 g of crude clevidipine butyrate and 100 ml isopropanol were charged in a 250 ml flask and stirred at reflux temperature (80-82° C.) until a clear solution was obtained. Afterwards, the solution was cooled down to 30-40° C. and 80 ml of DM water were slowly added and stirred for 3 hours at 25-30° C. The solid was filtered, washed with 20 ml of an isopropanol:water solution (50% v/v) and dried yielding 15.9 g of wet clevidipine butyrate (LOD=44.6%). Yield (on dry basis): 8.8 g, HPLC purity: 99.49%, % Recovery: 88%.

Example 12

$2^{nd}$ Purification of Clevidipine Butyrate 15 g of wet clevidipine butyrate (LOD: 44.6%) and 90 ml of isopropanol were charged in a 250 ml flask. The mass was heated up to 80-82° C. until a clear solution was obtained. 0.4 g of activated charcoal were added to the clear solution and stirred for 30 minutes at 80-82° C. Afterwards, the solid was filtered out, while still hot, by means of a hyflow bed. The filtrate was transferred a 250 ml flask and 80 ml of DM water were slowly added inducing the precipitation of clevidipine butyrate. The obtained mixture was stirred at 25-30° C. for 3 hours. The precipitate was filtered and washed with 20 ml of a 50% solution of isopropanol:water (v/v). The wet cake was dried under reduced pressure for 8-10 hours at 50-55° C., until constant weight was achieved, yielding 6.8 g of a white solid (LOD<0.5%). % Recovery: 81.8%, HPLC purity: 99.62%.

m.p. by DSC: 138.8° C.

Clevidipine butyrate form A

Example 13

Purification of Crude Clevidipine Butyrate 10 g of crude clevidipine butyrate and 100 ml acetone were charged in a 500 ml flask and stirred for 10 minutes until clevidipine butyrate is completely dissolved. 80 ml of DM water were slowly added and stirred at 25-30° C. for 3 hours. The solid was filtered and washed with 20 ml of an acetone: water solution (50% v/v) yielding 14.6 g of wet clevidipine butyrate (LOD: 42%). Yield (on dry basis): 8.46 g, HPLC purity: 99.73%, % Recovery: 84.6%.

Example 14

$2^{nd}$ Purification of Clevidipine Butyrate 14.6 g of wet clevidipine butyrate and 85 ml acetone were charged in a 250 ml flask and stirred until the solid was completely dissolved. 0.8 g activated charcoal were added to the reaction mass and stirred for 30 minutes at 25-30° C. Afterwards, the solid was filtered through a hyflow bed and the collected filtrate charged in a 250 ml flask. 68 ml of DM water were slowly added to the collected filtrate inducing the precipitation of clevidipine butyrate. The obtained mixture was stirred at 25-30° C. for 3 hours. The solid was filtered and washed with 20 ml of a 50% solution of acetone:water (v/v). The wet cake was dried under reduced pressure at 50-55° C. for 8-10 hours, until constant weight was achieved (LOD<0.5%). Yield 7.1 g % Recovery: 83.9%, HPLC purity: 99.88%, m.p. by DSC: 138.9° C.

Clevidipine butyrate form A

Example 15

Purification of Clevidipine Butyrate 5 g of clevidipine butyrate (HPLC purity 99.88%) and 50 ml methanol were charged in a 250 ml flask. The mixture was stirred for at 55-60° C. until a clear solution was obtained. Afterwards, the solution was cooled down to 35-40° C. and 40 ml of DM water were slowly added. The mixture was stirred at 25-30° C. for 3 hours. The solid was filtered and washed with 25 ml of a 50% (v/v) solution of methanol:water. The wet cake was dried under reduced pressure at 50-55° C. for 8-10 hours to yield 4.5 g of a white solid. HPLC purity: 99.91, % Recovery: 90%.

m.p. by DSC: 142.8° C.

Clevidipine butyrate form B

Example 16

Purification of Clevidipine Butyrate 1 g of clevidipine butyrate (HPLC purity 99.88%) and 10 ml methanol were charged in a 100 ml flask. The mixture was stirred for at 55-60° C. until a clear solution was obtained. Afterwards, the solution was cooled down to 35-40° C. and 8 ml of DM water were slowly added. The mixture was stirred at 25-30° C. for 3 hours. The solid was filtered and washed with 5 ml of a 50% (v/v) solution of methanol:water. The wet cake was dried under reduced pressure at 50-55° C. for 8-10 hours to yield a 0.9 g of a white solid. HPLC purity: 99.91, % Recovery: 90%.

m.p. by DSC: 143.7° C.

Clevidipine butyrate mixture of form A and form B

Priority is claimed to U.S. 61/332,446, filed on May 7, 2010, the subject matter of which is incorporated by reference.

The invention claimed is:
1. A process for the preparation of clevidipine butyrate comprising the step:
(i) reacting a compound of formula (I):

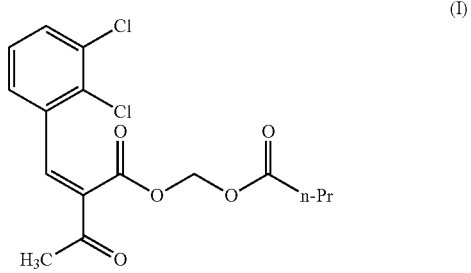

with methyl 3-amino crotonate to obtain clevidipine butyrate, wherein the step (i) is carried out in the presence of an organic solvent or a solvent mixture comprising an organic solvent.

2. The process according to claim 1, wherein the mole ratio of methyl 3-aminocrotonate to compound of formula (I) is from about 2:1 to 1:2, from 1.25:1 to 1:1.25, or about 1:1.

3. The process according to claim 1, wherein the step (i) is carried out at a temperature below about 150° C.

4. The process according to claim 1, wherein the organic solvent is selected from methanol, ethanol, iso-propyl alcohol, n-propanol, tert-butanol, acetone, methyl ethyl ketone, methyl tert-butyl ether, ethyl acetate, methyl acetate, propyl acetate, isopropyl acetate, butyl acetate, isobutyl acetate, diisopropyl ether toluene, methyl cyclohexane, xylene, and mixtures thereof.

5. The process according to the claim 1, wherein the organic solvent is selected from ethanol, isopropyl alcohol, n-propyl alcohol, diisopropyl ether, and mixtures thereof.

6. The process according to claim 1, wherein the compound of formula (I) is prepared by esterifying a compound of formula (II) or a salt thereof:

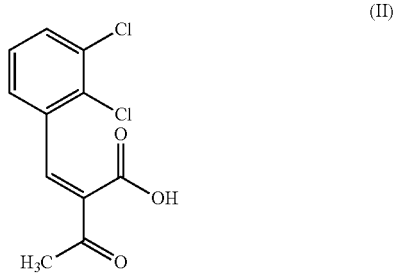 [SMILES: CC(=O)/C(=C/c1cccc(Cl)c1Cl)C(=O)O]

with a compound of formula L-CH$_2$OCO-n-Pr, wherein L is a leaving group.

7. The process according to claim 6, wherein the leaving group is a carboxyl ester, a halogen, or a sulfonyloxy group represented by —OSO$_2$R$_2$, wherein the R$_2$ is alkyl, p-toluoyl, trifluoromethyl or fluorine.

8. The process according to claim 6, wherein the leaving group is selected from trifluoromethylsulfonyl, para-nitrobenzenesulfonyl, para-toluenesulfonyl, methylsulfonyl, trifluoroacetyl, para-nitrobenzoyl, para-methylbenzoyl, acetyl, iodine, bromine, chlorine, and fluorine.

9. The process according to claim 6, wherein the esterifying occurs in the presence of at least one organic and/or inorganic base.

10. The process according to claim 6, wherein the compound of formula (II) is obtained by hydrolyzing the compound of formula (III),

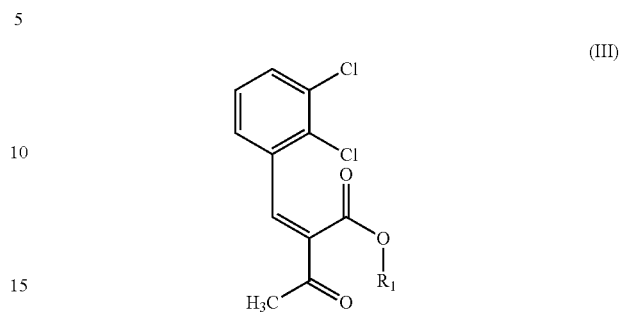

wherein R$_1$ is selected from an alkyl; an aryl; and an alkaryl.

11. The process according to claim 6, wherein R$_1$ is selected from methyl, ethyl, propyl, isopropyl, butyl, tert-butyl, phenyl, benzyl, and trityl.

12. The process according to claim 10, wherein the compound of formula (III) is obtained by reacting 2,3-dichlorobenzaldehyde, compound of formula (IV), with CH$_3$—CO—CH$_2$—COOR$_1$, compound of formula (V), and by adding a base and/or an acid:

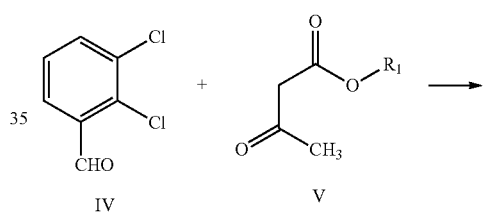

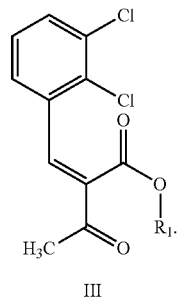

13. The process according to claim 11, wherein the compound of formula (III) is obtained by reacting 2,3-dichlorobenzaldehyde, compound of formula (IV), with CH$_3$—CO—CH$_2$—COOR$_1$, compound of formula (V), and by adding a base and/or an acid:

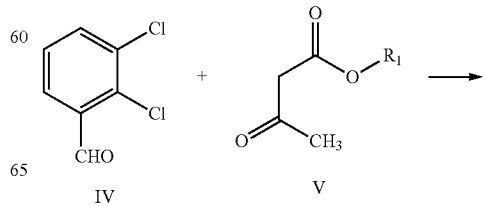

-continued

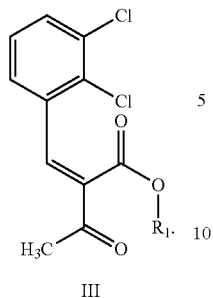

III

14. A crystalline polymorph clevidipine butyrate form A that exhibits an X-ray powder diffraction pattern having characteristic peaks expressed in degrees 2-theta at approximately 8.5 ±0.2, 16.2 ±0.2, 18.7 ±0.2, 22.1 ±0.2, 24.8 ±0.2, 25.4 ±0.2, 25.8 ±0.2, 27.7 ±0.2.

15. A crystalline polymorph clevidipine butyrate form B that exhibits an X-ray powder diffraction pattern having characteristic peaks expressed in degrees 2-theta at approximately 7.2 ±0.2, 9.0 ±0.2, 10.3 ±0.2, 17.0±0.2, 20.2 ±0.2, 21.9 ±0.2, 22.6 ±0.2, 22.9 ±0.2, 24.2 ±0.2, 25.4 ±0.2.

* * * * *